United States Patent [19]

McElfresh et al.

[11] Patent Number: 5,478,505
[45] Date of Patent: Dec. 26, 1995

[54] AIR TREATING DEVICE

[75] Inventors: Mark McElfresh, Scottsdale, Ariz.;
Jim F. Warner, 300 Cathedral Pkwy. 15H, New York, N.Y. 10026; Young C. Park, 255 Second St., Palisades Park, N.J. 07650; Charles A. Curtiss, 35-14 33rd St. 2R, Astoria, N.Y. 11106; Martin Bogenstaerter, Hubertusstrasse 1, 80639 Munich, Germany

[73] Assignees: Jim F. Warner, New York, N.Y.; Young C. Park, Palisades Park, N.J.; Charles A. Curtiss, Astoria, N.Y.; Martin Bogenstaerter, Munich, Germany; Mark McElfresh, Scottsdale, Ariz.

[21] Appl. No.: 275,216

[22] Filed: Jul. 14, 1994

[51] Int. Cl.$^6$ ............................... B01F 3/04
[52] U.S. Cl. ............... 261/30; 261/104; 261/DIG. 65; 422/124; 239/57
[58] Field of Search .............. 261/DIG. 65, 30, 261/104; 422/124; 239/34, 57

[56] References Cited

U.S. PATENT DOCUMENTS

| | | | |
|---|---|---|---|
| 1,614,817 | 1/1927 | Andrew | 422/124 |
| 1,757,530 | 5/1930 | Keim | 239/57 |
| 2,141,402 | 12/1938 | Muller | 239/36 |
| 2,351,267 | 6/1944 | Irwin | 239/57 |
| 2,673,120 | 3/1954 | Bink et al. | 239/57 |
| 4,055,672 | 10/1977 | Hirsch et al. | 426/127 |
| 4,145,001 | 3/1979 | Weyenberg et al. | 239/56 |
| 4,157,787 | 6/1979 | Schwartz | 239/56 |
| 4,161,284 | 7/1979 | Rattan | 239/43 |
| 4,306,679 | 12/1981 | Dusek et al. | 239/59 |
| 4,356,969 | 11/1982 | Obermayer | 239/6 |
| 4,374,571 | 2/1983 | Hirvela | 239/36 |
| 4,523,870 | 6/1985 | Spector | 261/DIG. 65 |
| 4,583,686 | 4/1986 | Martens et al. | 239/35 |
| 4,634,614 | 1/1987 | Holzner | 428/35 |
| 4,753,389 | 6/1988 | Davis | 239/6 |
| 4,808,347 | 2/1989 | Dawn | 261/30 |
| 4,814,212 | 3/1989 | Spector | 428/14 |
| 4,840,773 | 6/1989 | Wade | 261/DIG. 65 |
| 4,849,606 | 7/1989 | Martens et al. | 219/271 |
| 4,948,047 | 8/1990 | Zembrodt | 239/34 |
| 4,960,240 | 10/1990 | McElfresh | 239/56 |
| 4,968,456 | 11/1990 | Muderlak et al. | 261/30 |
| 5,004,138 | 4/1991 | Gabas | 224/312 |
| 5,230,867 | 7/1993 | Kunze et al. | 422/123 |
| 5,234,162 | 8/1993 | Sullivan | 239/56 |
| 5,269,723 | 12/1993 | Bender | 454/157 |
| 5,282,571 | 2/1994 | Smith et al. | 239/54 |
| 5,383,598 | 1/1995 | Styles | 239/57 |

FOREIGN PATENT DOCUMENTS

| | | | |
|---|---|---|---|
| 816578 | 5/1937 | France | 239/57 |
| 2251601 | 7/1992 | United Kingdom | 239/57 |

OTHER PUBLICATIONS

GLADE Clip–Ons package (S. C. Johnson & Son, Racine, Wis.) (Date Unknown).

*Primary Examiner*—Tim R. Miles
*Attorney, Agent, or Firm*—Bernard L. Howard

[57] ABSTRACT

An air-treating article for dispensing a volatilizable material, such as air freshener fragrance, into the atmosphere of an enclosed area, such as an automobile interior. The device includes a housing and a reservoir of the volatilizable material therein, and also includes a dual-configured, articulating attachment clip which enables attachment of the device at a high-air-flow station, such as the forced air vent grille of the automobile, or at a low-air-flow station, such as the sun visor of the vehicle. The device enables use of the consistent delivery rates of a low-density polyethylene membranes while at the same producing a higher delivery rate than normally achieved with such membranes.

17 Claims, 3 Drawing Sheets

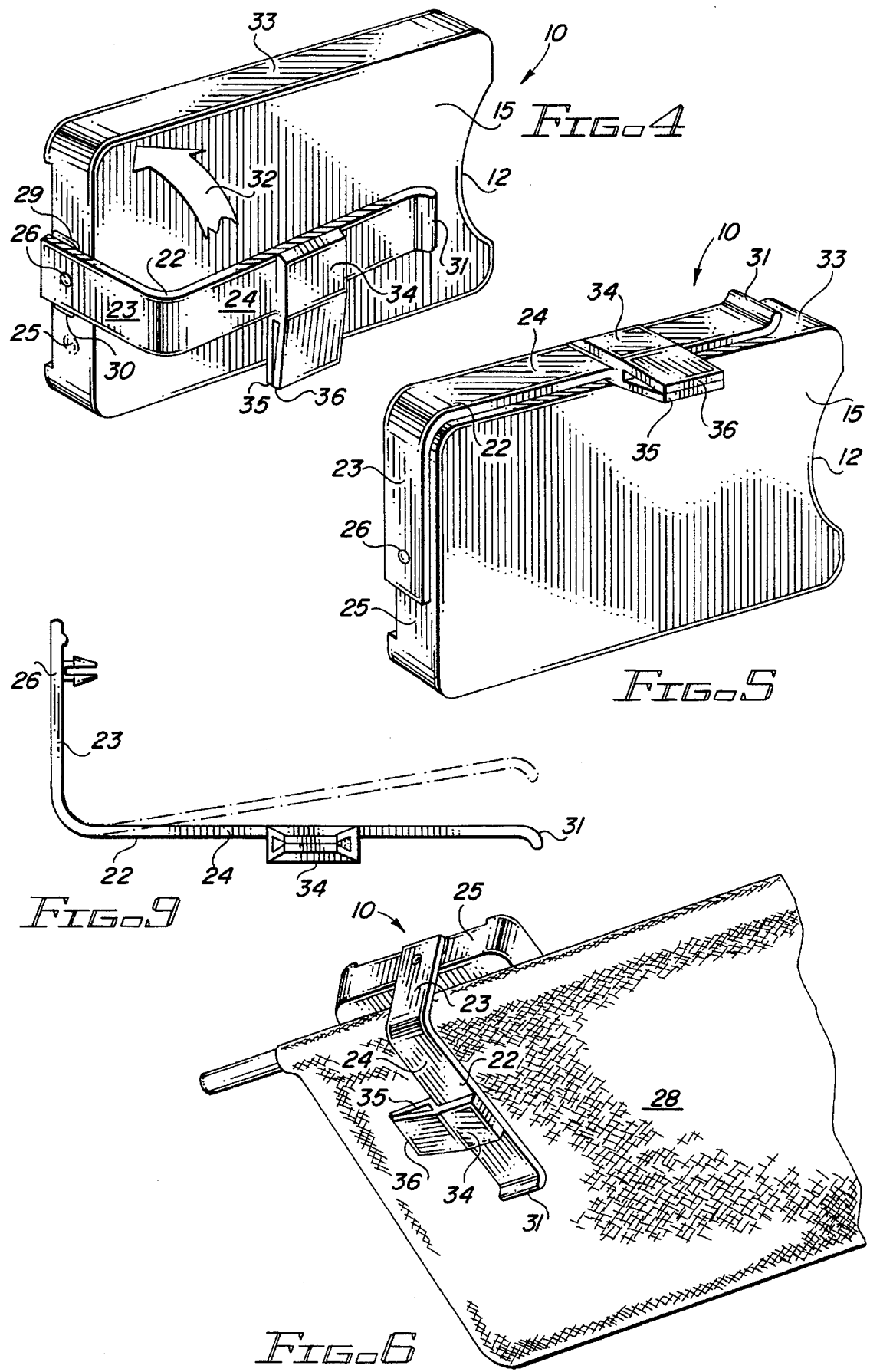

AIR TREATING DEVICE

BACKGROUND OF THE INVENTION

The present invention relates generally to dispensers of volatilizable materials. More particularly, the invention relates to air fresheners for dispensing fragrant and/or deodorizing compositions in an enclosed area, such as the interior of a vehicle.

Currently existing air fresheners for vehicle interiors typically consist of a fragrance delivery system and a means for attaching the delivery system to the interior of the vehicle. The majority of these delivery systems use a cellulose pad saturated with perfume which, when exposed to the atmosphere, delivers fragrance via evaporation. The rate determining step for these delivery systems is evaporation from the pad.

Since Ficke's law teaches delivery rate from evaporation is dependent upon concentration, these systems deliver materials at an inconsistent rate, following first-order kinetics. This leads to very high levels of fragrance initially and an unacceptably low level of fragrance after only a short period of time.

The ideal air freshener delivery system would follow zero-order kinetics and have a delivery rate constant over time. This is difficult because perfumes typically have fifty to one hundred or more components, each with unique vapor pressures. The variation in vapor pressure causes each component to diffuse into the atmosphere at different rates. Approaching the ideal state is attainable by using transport phenomenon other than evaporation as the rate controlling step. One such system currently available is a low-density polyethylene membrane hermetically sealed to a reservoir. This type of system uses diffusion of the perfume's components through the membrane to greatly improve consistency of delivery over time. The drawback to these systems is the reduced delivery initially is too low to provide adequate performance.

It is an object of the present invention to provide a dispensing device which utilizes the consistent delivery of a membrane system but at the same time provides the user with the ability to increase or decrease intensity of delivery, as conditions require, throughout the life of the product.

It is another object of the invention to provide dispensing means which enable the user initially to dispense the perfume at a high rate of release to rapidly bring the aroma concentration within the interior of the vehicle up to a desired level and then to lower the rate of release to maintain the aroma concentration at the desired level.

It is a further object to provide a simple, uncomplicated dispensing device which can be manufactured economically from standardly available materials and which can be used immediately without the need for extensive directions.

Other objects and advantages will become apparent as the specification proceeds.

SUMMARY OF THE INVENTION

The present invention is based on the concept of placing the perfume and the membrane delivery system in a unique housing having an articulating, dual-function attachment clip which enables the user to place the dispenser in a position to use the vehicle's ventilation system to increase delivery, or to place the unit on a sun visor or other similar location where less air flow exists, when less freshening is desired. By providing the user with the ability to use the housing unit on the forced air ventilation vent or in a quieter position, such as on a sun visor, the ability to customize the level of fragrance delivery to the user's desire is achieved.

The invention therefore comprises a combination dispensing structure including a housing and a reservoir of volatilizable material contained therein, said article being adapted for removable attachment to a high-air-flow station for high-level release and/or distribution of the volatilizable material and being also adapted for removable attachment to a low-air-flow station for low-level release and/or distribution of said material.

In its preferred embodiment, the invention relates to a dual-configured, articulating attachment device for removably fastening an air freshener at selected locations, comprising (a) a housing adapted to contain a reservoir of volatilizable fragrance, said housing comprising front and rear walls connected by side and end walls; (b) an opening in said front wall through which said fragrance released from said reservoir may reach the surrounding atmosphere; (c) a generally L-shaped fastening clip, a first leg of which is pivotally mounted on an end wall of said housing, and a second leg of which is provided with a pair of cooperating flexible elements adapted to engage a vane of a forced air vent grille; said L-shaped fastening clip being adapted for swingable motion between (i) a first attachment configuration in which the said flexible elements on said second leg are in a position to engage a vane of a forced air grille to cause the said rear wall of said housing to face the flow of forced air through said grille and (ii) a second attachment configuration in which said second leg and said rear wall of said housing are positioned to grip a projection, such as a sun visor, between them by spring action, for attachment of the air freshener to said projection.

The invention is based in part on the discovery that, when the dispenser is placed in the forced air stream exiting through the ventilation grille, it is not necessary that the air stream pass through the dispenser in order to dispense fragrance into the air stream. Thus, it has been found that, if the back surface of the dispenser housing which faces the air flow exiting through the grille is impermeable to the flow of air, and if the front surface facing away from the flow of air comprises a polyethylene delivery membrane, then the air exiting the grille will flow around the housing and lift a given quantity of perfume from the face of the membrane as it passes by. However, in another embodiment, it has been found that, if the positions of the front and back surfaces are reversed in the air stream, substantially equivalent results are obtained.

The invention therefore further comprises a combination structure including a substantially rectilinear housing and a reservoir of volatilizable material such as perfume therein; said combination structure providing a first surface which is substantially impermeable to the flow of air in said air stream, and a second, permeable surface, from which volatilizable material is dispensed from said reservoir into said air stream; whereby the air in said air stream is forced to flow around said combination structure while lifting volatilizable material from the permeable surface thereof, thereby allowing dispersion of said material into said air at a controlled rate of release.

The invention also relates to the method of freshening air in an enclosed area such as a vehicle interior, comprising the steps of providing an air freshener of the nature described above, initially attaching the freshener at a high-air-flow station, such as a forced air vent grille, to increase the rate of fragrance release and thereby rapidly increase fragrance concentration in said enclosed area to a specified level, and subsequently attaching the air freshener at a low-air-flow station, such as a sun visor, to reduce the rate of fragrance release and thereby maintain fragrance concentration in the enclosed area at said specified level.

BRIEF DESCRIPTION OF THE DRAWINGS

The objects, features and advantages of the invention will be apparent to those skilled in the art from the following detailed description, taken together with the accompanying drawings, in which:

FIG. 4 is a perspective view of the device, with the clip positioned for attachment to an automobile sun visor.

FIG. 5 is a perspective view of the device, with the clip positioned for attachment to an automobile air vent grille.

FIG. 6 is a perspective view showing actual attachment of the device to a sun visor.

FIG. 9 is side view of the spring clip, showing the first and second legs thereof urged to the 90 degree angle position, but with the normal 82 degree angle shown in dotted lines.

DETAILED DESCRIPTION OF THE INVENTION

The features of the present invention can be used for treating the air in any enclosed area with any suitable volatilizable treatment medium. However, for simplification of the description and without limiting the scope of the invention, the invention will be described in relation to the dispensing of air freshening fragrances in the interior of an automobile.

Figure 1:
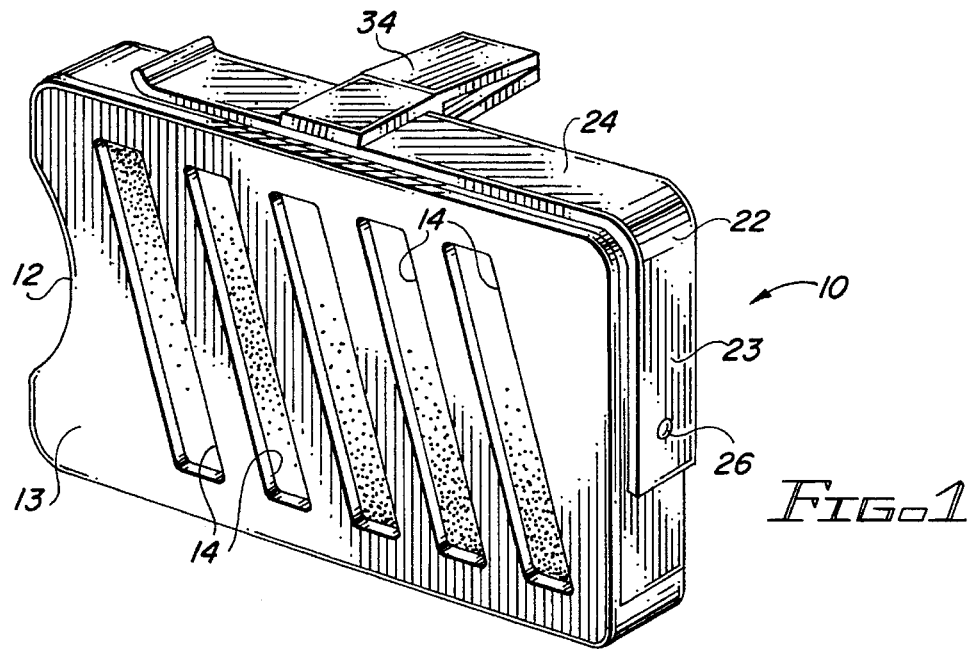
FIG. 1 is a perspective view of the air treating device of the present invention, showing the dual-action attachment clip.
Figure 2:
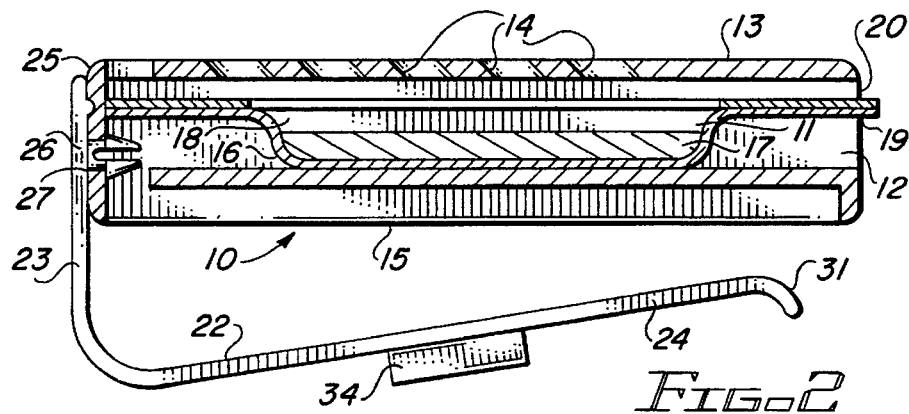
FIG. 2 is a cross-sectional elevational view of the device, showing the housing, it contents, and the attached spring clip.
Figure 3:
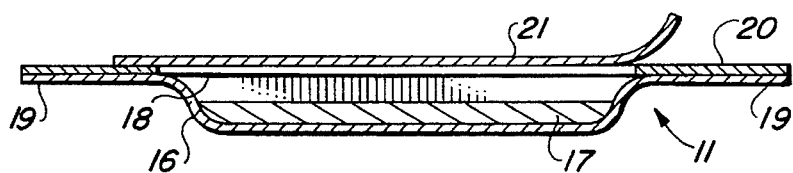
FIG. 3 is a cross-sectional side view of the fragrance reservoir, showing the fragrance contained therein and the dispensing membrane sealed to the reservoir.

Referring to the drawings, the device of the invention includes a housing generally designated by the numeral 10 (see FIGS. 1 and 2) which contains a removable fragrance cartridge or reservoir generally designated by the numeral 11 (see FIGS. 2 and 3). As shown, housing 10 is a hollow, rectangular holder having an open end 12 for receiving the fragrance cartridge 11, and it also has a front face 13 provided with vent openings 14 through which fragrance vapors from cartridge 11 may be diffused into the atmosphere (see FIGS. 1 and 2). Housing 10 has a rear face 15 which is impermeable to the flow of air (see FIGS. 2, 4 and 5). The housing may be made from any suitable material and, in the preferred embodiment, is injection molded from a thermoplastic material such as polypropylene.

As shown in FIGS. 2 and 3, a substantially flat, rectilinear fragrance cartridge 11, which may be of the replaceable type, includes a tray or container 16 for storing a quantity of perfume or other air freshener material 17 which is to be volatilized into the atmosphere in the operation of the device. Container 16 has an opening 18 at its upper end, which is surrounded by a peripheral flange 19. A permeable membrane 20 is sealed to the upper surface of the flange 19 and provides a cover over the opening 18. Adhered to the outer surface of membrane 20 is an impermeable strip 21 which prevents dispensing of vapors of the material 17 through membrane 20 until after its removal. Membrane 20 is permeable to the volatile material 17, such that, after removal of strip 21, material 17 migrates through membrane 20, to the surface thereof, and is dispensed to the atmosphere as an air-treating vapor.

The volatile material 17 may be the liquid or gel form of any of the volatile fragrances normally used for room air fresheners and may contain various mixtures of essential oils and the like, such as mint, floral, lemon-lime and the like. The membrane 20 may be any of the available low-density polyethylene films which permit consistent diffusion of the perfume's components through the membrane. Such membranes operate generally on a molecular level gas diffusion principle, as opposed to a bulk transport of vapor or liquid principle.

An inventive feature of the invention is a dual-configured, articulating attachment clip 22 which is pivotally attached to housing 10 and is adapted for swingable motion between a first attachment configuration for removable positioning of housing 10 and its contents at a high-air-flow station, such as a forced air vent grille, and a second attachment configuration for removable positioning of the device at a low-air-flow station, such as a sun visor. As shown in FIGS. 4, 5, 6 and 7, the clip 22 is generally L-shaped, having a first leg 23 and a second leg 24. The first leg 23 is pivotally mounted on the closed end wall 25 of the housing 10, thereby enabling clip 22 to swing between a sun visor attachment position, as shown in FIG. 4, to a vent grille attachment position, as shown in FIG. 5. Any known pivoting fastener may be used for mounting the clip 22 to the housing 10. In the embodiment shown in FIGS. 2 and 9, the mounting is accomplished with a compressible pivot pin 26 which is formed as an integral part of leg 23 and which snaps into a properly sized hole 27 in the end wall 25.

In the sun visor attachment position shown in FIGS. 4 and 6, the sun visor 28 is gripped between the second leg 24 of the clip 22 and the back wall 15 of the housing 10. To provide the necessary gripping action, it is desirable that the clip 22 be made of a flexible material which allows the clip to be spread open to receive the sun visor but which has memory characteristics urging the clip back to a default position. Any suitable plastic which may be injection molded or thermoformed may be used for this purpose. Other materials, such as metal, are also useful. A preferred material is injection-molded Delrin acetal which has excellent mechanical properties ideally suited to this type of application. As shown in FIGS. 2 and 9, the default angle between legs 23 and 24 should be somewhat less than 90 degrees, so that when the clip is spread to a 90 degree angle the memory characteristics of the material assist in the gripping action. An angle generally in the range from 80 to 85 degrees has been found suitable for purposes of the present invention.

As will be seen from the drawings, in the sun visor attachment position, end wall 25 and first leg 23 are in substantially the same plane, but the longitudinal axes of these two elements are substantially perpendicular to each other. To maintain this perpendicular relationship, it is desirable to provide the surface of end wall 25 with locking nubs 29 and 30 which act in cooperation with the edges of leg 23 to prevent movement out of alignment with the perpendicular. Other means, such as cooperating beads and detents (not shown) may be used. The leading edge 31 of leg 24 is beveled to assist in spreading the clip to an open position to grasp the visor 28.

To move to the vent grille position, the clip 22 is swung in the direction shown by the arrow 32 in FIG. 4 and thus assumes the position shown in FIG. 5. In this position, the first and second legs 23 and 24 of clip 22 are aligned with and generally conform to the configuration, respectively, of the end wall 25 and the adjacent side wall 33 of the housing 10. To achieve this position, the angle between legs 23 and 24 must be forced from its default value to about 90 degrees, and the spring force which is thus created from polymer memory tends to hold the clip 22 snugly and firmly in the aligned position shown in FIG. 5.

Figure 7:
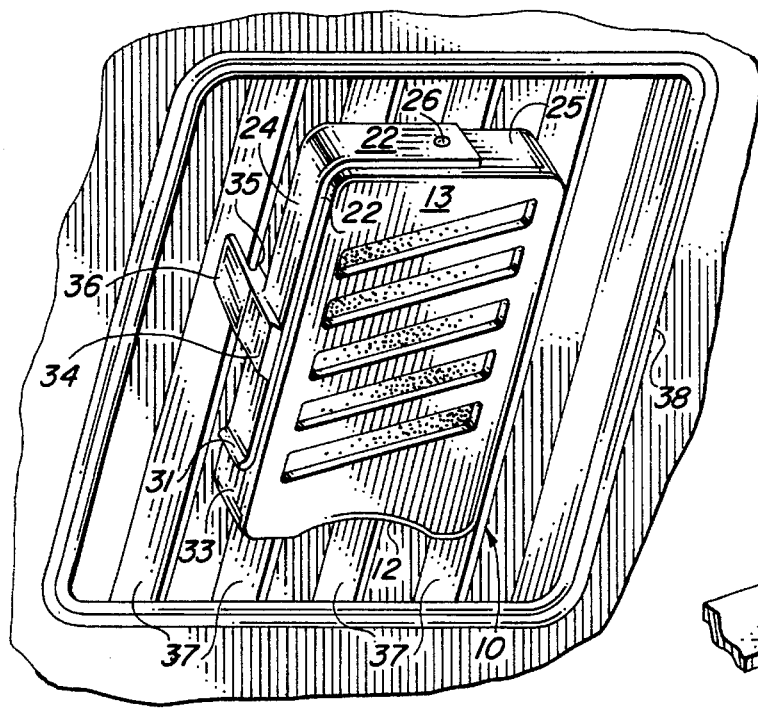
FIG. 7 is a perspective view showing actual attachment to a ventilation vent grille.

As shown in the drawings, leg 24 is provided with side-projecting vent clip 34 which includes two resilient flat tongs 35 and 36 adapted for gripping the vanes or louvers or slats 37 of an automobile forced air vent grille 38. When the clip 22 has been moved to the vent grille position, as shown in FIGS. 5 and 7, the tongs 35 and 36 are in a position to grasp a vent grille slat 37 in the manner shown in FIG. 7, so that the rear face 15 of housing 10 faces in an up-stream direction into the flow of forced air coming through the grille 38. As shown, the second leg 24 and the vent clip 34 are in substantially the same plane, but the longitudinal axes of these two elements are substantially perpendicular to each other. Although FIGS. 1, 5, 7 and 11 show the rear face 10 facing in the upstream direction, it has been found that equally effective results can be obtained if the positions are reversed so that the front face 13 faces in the upstream direction, as will be hereinafter described.

The distance between the inner surfaces of tongs 35 and 36 should be chosen to provide an effective fit with the slats or vanes 37 in the vent grilles of the majority of automobiles. To provide information for this aspect of the invention, the vent grilles of the top fifteen selling cars in the United States (Source: September 1992 Motor Trend Ward's Automotive Yearbook) were measured. The following Table 1 shows the target as well as maximum and minimum dimensions for the space between the two inner surfaces of tongs 35 and 36:

TABLE 1

| Vent Vane Dimensions | | |
| --- | --- | --- |
| Front Vane Thickness: | | |
| Thinnest vane: | .031 in. | (0.79 mm) |
| Thickest vane: | .210 in. | (5.28 mm) |
| Average: | .080 in. | (2.03 mm) |
| Front Vane Spacing: | | |
| Closest spacing: | .218 in. | (5.54 mm) |
| Widest spacing: | .470 in. | (11.94 mm) |
| Average: | .352 in. | (8.94 mm) |
| Front Vane Depth Dimensions: | | |
| Largest: | .75 in. | (19.05 mm) |
| Smallest: | .080 in. | (2.03 mm) |

TABLE 1-continued

| Vent Vane Dimensions | | |
| --- | --- | --- |
| Average: | .125 in. | (3.18 mm) |

Figure 10:
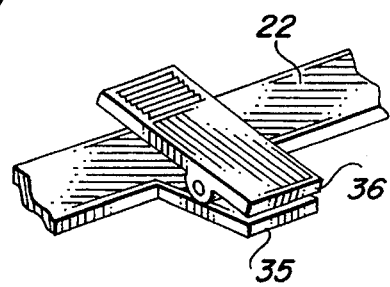
FIG. 10 is a perspective view of a special alligator clip embodiment of the grille vane gripping clip of the invention.
Figure 8:
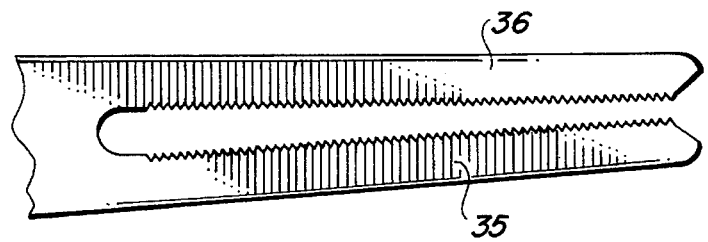
FIG. 8 is an enlarged side view of the grille vane engaging tongs, showing the serrated inner surfaces thereof.
Figure 11:
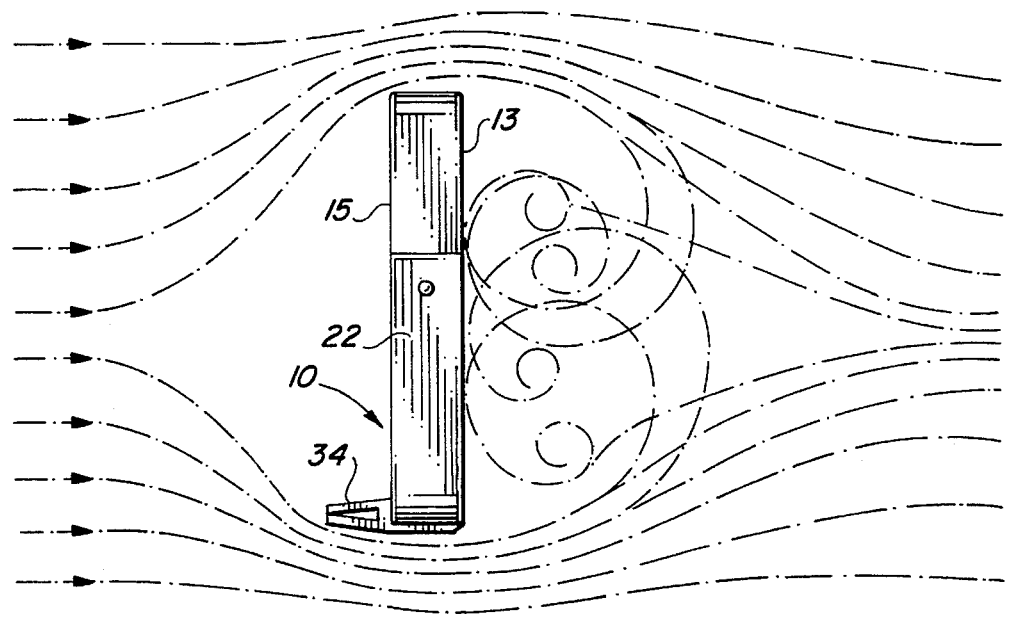
FIG. 11 is a schematic drawing of the lines of air flow created when the device of the present invention is attached to the vent grille of an automobile ventilating system.

In the preferred embodiment of the invention, the inward facing walls of the tongs 35 and 36 should be spaced apart from 0.76 mm at the opening to 1.54 mm at the root of the clip. This spacing allows the clip to fit the majority of cars. The opening should increase from the open end to the root, in order to allow the inner surfaces of the tongs to move to a parallel orientation to the vent grille vane as the tongs are spread open. This provides the maximum surface area for holding onto the vent grille vane. This also prevents the memory of the polymer and the geometry of the vent clip tongs 35 and 36 from creating a force which squeezes the grille vent vane from between the tong surfaces. As shown in FIG. 8, the inner surfaces of the tongs 35 and 36 should be serrated in order to reduce the contact area and thereby increase the holding pressure. For special purposes, it may be desirable to modify the spring clip 34 by providing an alligator spring activated metal clip for the tongs 35 and 36, as shown in FIG. 10.

Figure 12:
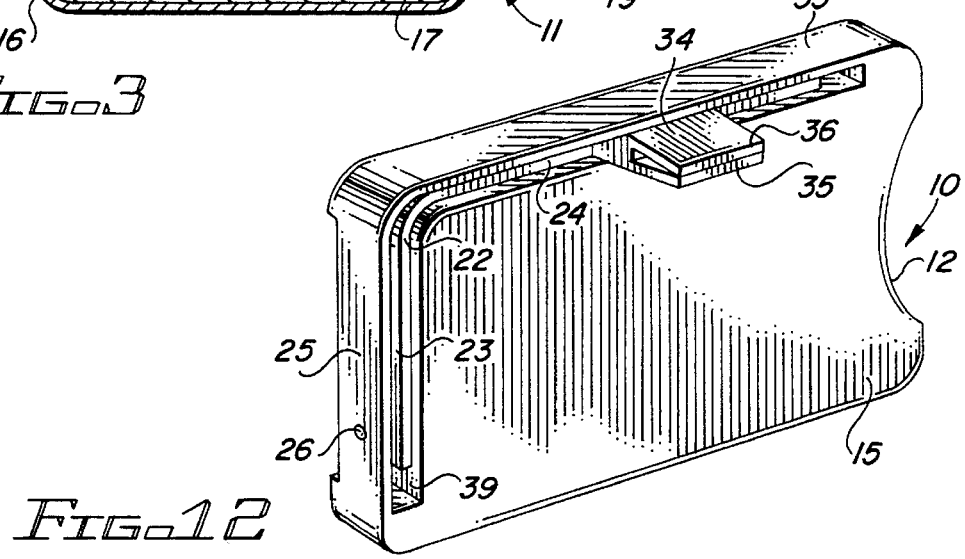
FIG. 12 is a perspective view similar to FIG. 5 but showing the clip positioned internally in the housing.

Although clip 22 may be mounted externally on the housing 10, as shown in FIGS. 1, 2, 4, 5, 6 and 7, an alternative embodiment is shown in FIG. 12, wherein the clip 22 is mounted internally. This is accomplished by providing an L-shaped slot 39 formed along the inner edge of end wall 25 and side wall 33 of housing 10. The L-shape of slot 39 mates with the L-shape of clip 22, so that clip 22 may reside in the recess of slot 39 when in the vent grille position, but may be swung on pivot 26 out to the sun visor position when desired.

In the operation of the invention, the user selects a fragrance cartridge 11 containing the desired fragrance, peels tile protective film 21 from the surface of the diffusion membrane 20, and inserts the cartridge into the housing 10, according to known procedures. If, in the initial use of the device in an automobile interior, there is little or no concentration of fragrance in the enclosed area, the preferred procedure will be to move the clip 22 to the vent grille position shown in FIGS. 5 and 7 and attach the device 10 to a vane 37 in one of the vent grilles 38 of the automobile. When the ventilation system is turned on, the forced air flow from the vent will cause rapid release of fragrance from the surface of the diffusion membrane 20, accompanied by a rapid distribution of this fragrance throughout the interior of the automobile. When the user senses that the appropriate level of fragrance has been reached, he or she can remove the device from the vent grille, swing the clip 22 to the sun visor position shown in FIGS. 4 and 6, and attach it to the sun visor 28 or other similar low-air-flow station, where the amount of fragrance emitting from the device will be at a reduced level but will provide the degree of emission necessary to maintain the fragrance concentration at the desired lower level. If changing conditions are encountered during the course of the user's stay in the vehicle, the ease of switching back and forth between the two positions facilitates maintaining a comfortable level of fragrance concentration, while at the same time avoiding wastage or overuse of the supply of fragrance. By providing the user with the ability to use the device on the sun visor or on the grille vent, the ability to customize the level of fragrance delivery to the user's desire is achieved.

The invention is based in part on the discovery that, when the dispensing device is attached to the air vent grille, it is not necessary for the air to flow through the device in order to produce effective distribution of fragrance into the atmosphere. A feature of the invention is that the rear wall 15 which faces the flow of air through the grille may be impervious to the flow of air. With this configuration, it has been found that the air currents will flow around the device and in doing so will create a turbulent negative pressure differential at the front face of the device, where fragrance vapors emitting from the surface of the membrane 20 are available to be taken up in said turbulent negative pressure differential and delivered into the atmosphere of the vehicle. See the diagram of FIG. 11.

It has also been discovered that, if the position of the device may be reversed so that the front face 13 faces the flow of air through the grille and the rear wall thus faces downstream, substantially the same results are obtained in terms of enhanced release and distribution of fragrance. In this reverse configuration, the impact of the air flow directly against the permeable membrane 20 causes a turbulence and depletion of fragrance from the surface of the membrane, which in turn increases the rate of molecular diffusion of fragrance from the reservoir through the membrane 20. Such fragrance released from the surface of the membrane is lifted by the air currents flowing around the device and thereby made available for distribution throughout the interior of the vehicle.

In either configuration, it is a feature that it is not necessary for the air to flow through the device. If it were required that the air flow through the device, then it would also be necessary to use a permeable cartridge, such as a porous pad saturated with the perfume. However, the high flow of air through such a structure would quickly deplete the supply of perfume. Further, as previously described, systems involving the evaporation of fragrance from porous pads deliver vapors at an inconsistent rate following first-order kinetics. In the present invention, the discovery that it is not necessary for the air to flow through the cartridge enables the use of the superior polyethylene membrane diffusion systems which more nearly approach zero-order kinetics. Although, the membrane diffusion system, as utilized in the present invention, normally produces a low delivery rate, the ability to expose the system to the air flow encountered in the automobile ventilation system enables a valuable increase in the delivery intensity when necessary.

In the present invention, the increased distribution of fragrance when the device is attached to the air vent grille is caused by dual phenomenon—namely, an increased migration through the membrane 20 and increased bulk transport of the released fragrance by reason of the action of the ventilation system fan which distributes the fragrance quickly throughout the interior of the automobile. The increased migration through the membrane is shown in the following example:

EXAMPLE 1

Two different air freshener perfumes (Fragrance A and Fragrance B) were evaluated under various air flow and temperature conditions over a period of 28 days to determine the amount of fragrance delivered from a perfume cartridge under the various conditions. The perfume cartridge, had generally the same configuration shown in FIG. 3, with a container 16, a quantity of perfume 17, and a permeable membrane 20 through which the perfume must migrate in order to be dispensed into the air.

Fragrance A and Fragrance B were tested in the presence of a forced air stream, and also in a quiet atmosphere, without forced air. A fan was used to create the forced air stream. In each test, the cartridge was tested with the air stream directed toward the front of the membrane and also with the air stream directed against the back of the unit. The amount of fragrance dispensed from the cartridge in each test was determined by capturing the released fragrance and weighing. The results after 28 days are shown in the following table:

| Perfume | Air Temperature (F.) | Air Flow/Direction | Delivery (Grams) |
|---|---|---|---|
| Fragrance A | 72 | Fan toward front | 0.85 |
| | 72 | Fan toward back | 0.78 |
| | 72 | No air flow | 0.56 |
| Fragrance B | 72 | Fan toward back | 1.26 |
| | 72 | No air flow | 0.75 |
| | 35 | No air flow | 0.08 |
| | 55 | AC air toward front | 0.79 |
| | 55 | AC air toward back | 0.78 |
| | 100 | Hot oven air toward front | 2.28 |
| | 100 | Hot oven air, no air flow | 2.03 |

The results indicate that air flow has the effect of increasing the release of fragrance through the membrane. The rate of release is substantially the same, whether the air flow is directed against the back of the unit or directly against the front of the membrane, the turbulence of air around the unit being sufficient to release and distribute the fragrance. Increased temperature has a significant effect on increasing the amount of fragrance released. Thus the operator of the automobile is able to obtain an initial increased distribution of fragrance throughout the interior of the automobile if the device is attached to the forced air vent grille with the heater on, as compared with having the air conditioning system providing the forced air through the vent grille.

Although preferred embodiments of the invention have been described herein in detail, it will be understood by those skilled in the art that variations may be made thereto without departing from the spirit of the invention.

What is claimed is:

1. An air-treating article for dispensing a volatilizable material into the atmosphere of an enclosed area, comprising a combination dispensing structure including a housing and a reservoir of volatilizable material contained therein, said article including a dual-configured, articulating attachment clip, which is pivotally attached to said housing and is adapted for swingable motion between a first attachment configuration for removable positioning of said article at a high-air-flow station in said area for high-level distribution of said volatilizable material and a second attachment configuration for removable positioning of said article at a low-air-flow station in said area for low-level distribution of said material.

2. An air freshening device for dispensing fragrance into the atmosphere in the interior of a vehicle, comprising:

(a) a housing having means defining an opening;

(b) a cartridge insertable in said housing through said opening, said cartridge containing a supply of said fragrance and having at least one wall made of a polymeric membrane enabling vapors of said fragrance to diffuse from said cartridge into the atmosphere in said vehicle; and (c) a dual configured, articulating attachment clip, which is pivotally mounted on said housing and is adapted for swingable motion between a first attachment configuration, for removable fastening of said air freshening device on a forced air vent grille in the interior of said vehicle, and a second attachment configuration, for removable fastening of said device on a sun visor in the interior of said vehicle.

3. A dual-configured, articulating attachment device for removably fastening an air freshener either to a vane of a forced air grille in a vehicle or to a sun visor in said vehicle, said device comprising:

(a) a housing adapted to contain a reservoir of volatilizable fragrance, said housing comprising front and rear walls connected by side and end walls;

(b) an opening in said front wall through which said fragrance released from said reservoir may reach the surrounding atmosphere;

(c) a generally L-shaped fastening clip, a first leg of which is pivotally mounted on an end wall of said housing, and a second leg of which is provided with a pair of cooperating flexible elements adapted to engage a vane of said forced air vent grille;

(d) said L-shaped fastening clip being adapted for swingable motion between (i) a first attachment configuration in which its said first and second legs are aligned with and conform to the configuration of, respectively, said end wall and an adjacent side wall of said housing, whereby the said flexible elements on said second leg are in position to engage a vane of said forced air grille to cause the said rear wall of said housing to face the flow of forced air through said grille and (ii) a second attachment configuration in which said second leg and said rear wall of said housing are positioned to grip said sun visor between them by spring action, for attachment of said air freshener to said sun visor.

4. A dual-configured, articulating attachment device for removably fastening an air freshener at selected locations, comprising:

(a) a housing adapted to contain a reservoir of volatilizable fragrance, said housing comprising front and rear walls connected by side and end walls;

(b) an opening in said front wall through which said fragrance released from said reservoir may reach the surrounding atmosphere;

(c) a generally L-shaped fastening clip, a first leg of which is pivotally mounted on an end of said housing, and a second leg of which is provided with a pair of cooperating flexible elements adapted to engage a vane of a forced air vent grille;

(d) said L-shaped fastening clip being adapted for swingable motion between (i) a first attachment configuration in which the said flexible elements on said second leg are in position to engage a vane of a forced air grille to expose said housing to the flow of forced air through said grille and (ii) a second attachment configuration in which said second leg and said rear wall of said housing are positioned to grip a projection between them by spring action, for attachment of said air freshener to said projection.

5. The attachment device as in claim 4 wherein said flexible elements on said second leg are in a position to engage a vane of a forced air grille to cause said rear wall of said housing to face the flow of air through said grille.

6. The attachment device as in claim 4 wherein said flexible elements on said second leg are in a position to engage a vane of a forced air grille to cause said front wall of said housing to face the flow of air through said grille.

7. The attachment device as in claim 4 wherein said fastening clip is injection molded.

8. The attachment device as in claim 4 wherein said fastening clip is made of Delrin acetal.

9. The attachment device as in claim 4 wherein said housing is made of polypropylene.

10. The attachment device as in claim 4 wherein the angle between said first and second legs of said fastening clip is less than 90 degrees, thereby producing a spring action when said legs are spread toward a 90 degree position to assume their first and second attachment configurations.

11. The attachment device as in claim 4 wherein said fastening clip is mounted externally on said housing.

12. The attachment device as in claim 4 wherein said fastening clip is mounted internally in said housing.

13. The attachment device as in claim 4 wherein said housing and said L-shaped fastening clip have cooperating locking means to retain said fastening clip in either the first or second attachment configuration.

14. The attachment device as in claim 13 wherein said locking means includes one or more nubs on said housing registering with one or more detents on said clip.

15. The attachment device as in claim 4 wherein said pair of flexible elements attached to said second leg of said clip lie in the same plane as said second leg but are perpendicular to the longitudinal axis of said second leg.

16. The attachment device as in claim 15 wherein said flexible elements comprise tongs having serrated inner surfaces.

17. The attachment device as in claim 15 wherein said flexible elements comprise a spring actuated metal clip.

* * * * *